United States Patent [19]

Cusato

[11] 3,986,265

[45] Oct. 19, 1976

[54] ORTHODONTIC TOOL FOR REMOVING EPOXY SECURED BRACKETS AND EPOXY RESIDUE

[75] Inventor: Anthony J. Cusato, Closter, N.J.

[73] Assignee: Henry Mann, Inc., Huntingdon Valley, Pa.

[22] Filed: June 9, 1975

[21] Appl. No.: 584,961

[52] U.S. Cl. .................................................. 32/66
[51] Int. Cl.² .......................................... A61C 7/00
[58] Field of Search ..................... 32/66, 40, 14 E

[56] References Cited
UNITED STATES PATENTS

| | | | |
|---|---|---|---|
| 3,209,458 | 10/1965 | Rosen | 32/40 R |
| 3,755,902 | 9/1973 | Northcutt | 32/66 |

Primary Examiner—Robert Peshock
Attorney, Agent, or Firm—Ralph R. Roberts

[57] ABSTRACT

This invention discloses an orthodontic tool for removing brackets fixed to teeth by an epoxy material and the residue material after removal of the brackets. This tool has prying and scraping jaws in which sharpened forward edges on the jaws are adapted for insertion behind the bracket and into the epoxy by which the bracket is applied. After the bracket is removed the epoxy may be scraped from the face of the tooth by the sharp front edges of the jaws of the tool. In addition to the jaw configuration of the tool, as depicted, there is also provided a molded plastic cap which is removably mounted upon one of the like jaws to permit positioning of this jaw upon the top of a tooth to provide a support against which the scraping or prying force action of the other jaw is moved. This plier is designed to remove the bracket and epoxy residue from the face of a tooth without damage to the tooth. For the convenience of retaining this removable plastic cap with the tool there is provided a spring clip means carried on the inside of one of the handles and upon this clip means the removable plastic cap is secured during the time both jaws of the tool are used for scraping and prying off of brackets.

7 Claims, 7 Drawing Figures

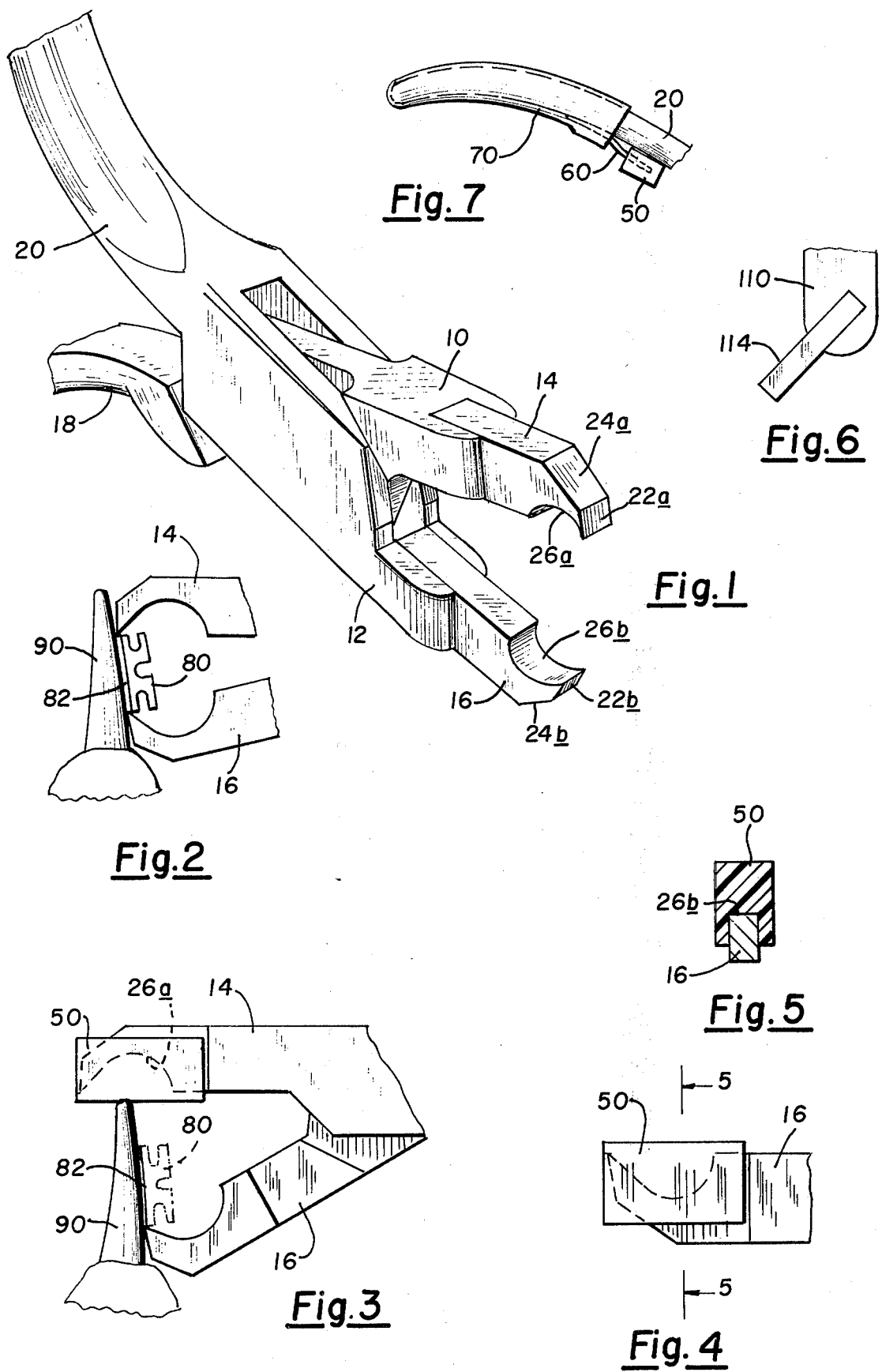

ORTHODONTIC TOOL FOR REMOVING EPOXY SECURED BRACKETS AND EPOXY RESIDUE

BACKGROUND OF THE INVENTION

1. Field of the Invention

With reference to the classification of art as established in and by the United States Patent Office the present invention is found in the general Class entitled, "Dentistry" (Class 32) and the subclass entitled, "orthodontic devices" (subclass 14R) and the further subclass entitled, "instruments" (subclass 40R).

2. Description of the Prior Art

Recently the practice of orthodontia has included the securing of brackets to teeth by epoxy cements. Orthodontists use these brackets to carry straightening wires. The securing of these brackets which may be of metal or plastic and which are attached by epoxy cement is an improvement in the resulting attachment of the brackets to the face of the tooth. Although the adhesion of the epoxy to the tooth surface is quite good, the removal of these brackets by conventional tools is extremely difficult due to the adhesion of the epoxy to the tooth.

The present tool is easily manipulated for removing the brackets by a prying action and the epoxy residue by a controlled scraping action. After removal of the brackets it is also necessary to remove a substantial portion of the epoxy cement residue by a scraping action. This scraping action is prior to a polishing action done by abrasive means.

In the present invention there is provided a plier-type device in which each of the jaws has sharpened forward edges on the jaws. These are preferably inserted portions which are made from hardened tool steel and ground to a very sharp chisel edge, of less than ninety degrees and as reduced to practice about sixty degrees. The inside of the forward jaw portions have arcuate configurations while the outer face extends to the sharp edge which permits a scraping or prying action to be performed by the sharp edges of the jaws as they are brought along or across the face of a tooth. In addition to a prying or scraping action provided by the jaw ends of the tool, it is contemplated that one of the jaws may provide a fulcrum means by adding to the jaw a plastic cap member of Teflon or nylon. This cap or support is formed so as to be tightly seated upon the cutout of one of the jaw members. This plastic cap provides a protective and cushioned surface which permits this jaw member to be positioned or placed upon the top of a tooth to give a pry base during the time the other jaw is used to remove a bracket or scrape the epoxy residue from the face of a tooth. In addition to providing this resilient cap or pad, there is provided on one of the handles a springclip device which is adapted to receive and retain this plastic insert during the time that it is not in use on the tool jaw.

SUMMARY OF THE INVENTION

This invention may be summarized at least in part with respect to its objects.

It is an object of this invention to provide, and it does provide, a bracket and an epoxy residue removing tool in which like hardened jaw members each have sharpened outer portions which are substantially parallel to the face of the other jaw. These sharpened jaws have their front edges formed with an acute angle of less than ninety degrees and provide therewith a sharp prying and scraping means.

It is a further object of this invention to provide, and it does provide, a plastic cap adapted to be seated upon one of these jaw members, this plastic cap member formed with seating means providing retention upon one of the jaw members. This resilient pad when mounted upon one of the jaws may be positioned at the upper edge or end of the tooth while the other jaw is brought against the face of the tooth to remove the bracket or scrape the epoxy residue from the tooth. When not in use this plastic cap is stored on a spring clip means provided on one of the handles.

The bracket and epoxy residue removing tool of this invention provides a plier-type instrument in which the jaws of the instrument are substantially identical. These jaw portions have their outer ends formed with comparatively flat faces disposed at a slight angle to a common plane when the jaws are brought together. The edges when brought together form a straight line which in one embodiment is parallel to the axis of the pivot of the jaws. In another embodiment the jaw inserts are at a 30° to 45° angle to the axis of the pivot of the handles. Each of the jaw ends are sharpened to provide a cutting edge and a chisel configuration. The inside of the jaws are preferably formed with an arcuate configuration which is combined with the outer face surface to provide an acute angle of less than 90° and preferably of an angle approximately 60°. The tool may have its jaws in alignment with the handle or preferably for ease of operation and use have the jaws disposed at an angle of 30° to 45° from the plane of the handle of the pliers.

In addition to the above summary the following disclosure is detailed to insure adequacy and aid in understanding of the invention. This disclosure, however, is not intended to cover each new concept therein no matter how it may later be disguised by variations in form or additions. For this reason there has been chosen a specific embodiment of the orthodontic pry tool as adopted for use in removing brackets and epoxy residue and showing two preferred jaw mountings in the handle members. These specific embodiments have been chosen for the purposes of illustration and description as shown in the accompanying drawings wherein:

BRIEF DESCRIPTION OF THE DRAWINGS

FIG. 1 represents a partly fragmentary, isometric view in an enlarged scale of the forward jaw portion of the tool and showing the bracket and epoxy residue removing jaws of this tool with the jaws in this arrangement being in a common plane with the handles;

FIG. 2 represents a partly fragmentary and diagrammatic side view showing the jaws of the tool of FIG. 1, the jaws positioned so as to pry from the face of the tooth a bracket attached by epoxy cement to the face of a tooth, these jaws ready to be moved toward each other to remove the bracket;

FIG. 3 represents the tool of FIG. 2 with a removable plastic protective cap mounted upon one of the jaws to allow this jaw to be positioned on the top edge of a tooth, the other jaw positioned to remove the residue and/or the bracket from the face of the tooth, the bracket is shown in phantom outline since it is assumed that this bracket has already been removed;

FIG. 4 represents a side view of the plastic protective cap placed upon the lower jaw;

FIG. 5 represents a sectional view taken on the line 5—5 of FIG. 4 and looking in the direction of the arrows;

FIG. 6 represents a fragmentary plan or top view in a reduced scale and showing a tool like that of FIG. 1 but with jaw inserts disposed to extend at an angle of approximately 45° to the plane of the handles, and FIG. 7 represents a somewhat fragmentary view of a handle portion of this tool in which a spring clip is attached to the underside of the handle, this clip adapted to engage and retain the protective plastic cap when not in use upon the jaw end of the tool.

In the following description and in the claims various details are identified by specific names for convenience. These names, however, are intended to be generic in their application. Corresponding reference characters refer to like members throughout the seven figures of the drawing.

This drawing discloses certain details of construction for the purpose of explanation but it should be understood that structural details may be modified in various respects and that the invention may be incorporated in other structural forms than shown.

BRACKET AND RESIDUE REMOVING TOOL OF FIGS. 1 THROUGH 5

Referring now in particular to the drawing there is depicted in FIG. 1 a bracket and residue removing tool of this invention. This tool includes upper and lower front jaw portions 10 and 12 in which are secured hardened inserts 14 and 16. As shown this is a pivoted plier-type tool in which handle portions 18 and 20 are continuations of the jaw portions 10 and 12. As reduced to practice, and shown, the inserts 14 and 16 are substantially identical or mirror images of each other. These inserts are of hardened tool steel and have short forward face portions identified as 22a and 22b. These face portions terminate with and at a beveled portion identified as 24a and 24b which then joins a rearwardly extending main body portion of the jaw. The inside portion of these jaws, adjacent the ends 22a and 22b, are formed with arcuate recess portions 26a and 26b which are seen in side view in FIGS. 2 and 3. The resulting jaw end is an acute angle sharpened edge of approximately 60° included angle. The forward edge of jaws 14 and 16 when brought together are contemplated to substantially align with each other although they move in a correspondingly arcuate path toward and away from each other.

As depicted in FIG. 6, jaws 114 and 116 are mounted in a body portion 110. These jaws are similar or identical to the jaws 14 and 16 of FIG. 1. Lower jaw 116 is not visible in this view since it is immediately below upper jaw 114. These jaws extend at an angle which is shown as approximately 45° leftwardly of the plane of the handle portions of the tool.

PROTECTIVE CAP SHOWN IN FIGS. 3, 4, 5 and 7

In FIGS. 3, 4, 5 and 7 there is depicted a molded plastic cap 50 which may be of nylon, Teflon (trademark of E. I. DuPont) or like material. This plastic cap has its inner surface molded to mate with and match the arcuate and side surfaces of the jaws 14 and 16. This inner configuration is a snug sliding fit upon the inner surface and the sides of the jaws so as to remain in place during the mounting and use of the plastic protective cap on this jaw. With jaws 14 and 16 being symmetrical and of like configuration and being arranged in the mirror image relationship, this cap 50 may be mounted on either of these jaws. Of course, the tool may be turned one hundred eighty degrees to provide the desired positioning of the plastic cap on a particular jaw. As shown in FIG. 7, this plastic protective cap when not in use may be stored on a spring clip 60 secured to the underside of the handle portion 20. This spring clip engages the jaw engaging molded relief formed in the plastic cap 50 and mounted on this spring clip this plastic cap is retained on the underside of the handle portion 20. As depicted, a handle sleeve 70 of plastic may be provided on the handle portion as a conventional convenience.

USE AND OPERATION

In the use and operation of the disclosed tool it is assumed that a bracket 80 which may be of metal or plastic is attached by means of an epoxy cement 82 to the front surface of a tooth 90. Such a cementing method is described in literature and display programs provided by GAC International, Inc., of 495 Smith, Street, Farmington, New York 11735 under their tradename, NUVA-TACH. This is a trademark for products of the L. D. Caulk Co. Metal or plastic brackets are cemented to the enamel surfaces of a tooth 90 by means of this technique employing epoxy cementing of brackets to teeth. When these brackets must be removed, care is required particularly where there are large or extensive restorations. The present tool permits the upper and lower edges of the bracket 80 to be engaged for prying by the sharpened chiseled edges of the jaws, as seen in FIG. 2. These jaw edge portions enter at or substantially near the face of the tooth 90 to pry the bracket from the face of the tooth. With the bracket removed the plastic protective protector 50 is mounted on that jaw which is to be placed on the upper or outer edge of the tooth 90 to provide a support for this tool. The unsupported jaw then provides a scraper which is easily manipulated by means of the jaw on which is mounted the plastic cap 50. This support allows careful manipulative action of the jaw to be made to scrape the epoxy residue from the face of the tooth. If desired or required, the plastic cap 50 may also be used as shown in FIG. 3 to remove a bracket 80 if a regular pry action as shown in FIG. 2 is not used or presents problems of removal of the bracket. After the bracket has been removed and the tool is manipulated with the plastic cap resting on top of the tooth, a careful manipulating and scraping action with the sharp edge of the jaw 16 enables the epoxy residue to be removed from the tooth and requiring only a very small amount of polishing action for the final cleaning of the tooth.

The jaws of this tool are shown as inserts which preferably are of hardened tool steel but, if desired, these jaws could be made as an integral extension of the handle members. The front face of the jaw can be flat or slightly curved but desirably this surface whether flat or slightly curved in one plane has its face terminating at the sharp edge. This permits resharpening and as a scraper, a scraper action having the closest approach to the tooth surface. The outer vertical edges of the flat face remain or are sharpened so as to provide additional scraping means where and when desired.

Terms such as "left," "right," "up," "down," "bottom," "top," "front," "back," "in," "out" and the like are applicable to the tool arrangements shown and described. These terms are merely for the purposes of description and do not necessarily apply to the position in which the tool may be constructed or used.

It is understood that modifications may be made within the scope of the accompanying claims and protection is sought to the broadest extent the prior art allows.

What is claimed is:

1. A plier-type orthodontic tool for the removal of a wire-retaining bracket and the residue of the attaching cement such as epoxy cement by which the bracket is secured to the side of a tooth, said tool including: (a) a pair of substantially plier-like jaws arranged in a mirror image relationship and conventionally maintained in a pivoted relationship by a hinge means; (b) a pair of handle means each operatively connected to a jaw member and adapted to move the connected jaw when these handle means are manipulated; (c) a hardened distal end portion formed on each jaw, each end portion having a short outer surface which terminates with a sharp chisel-like pry and scraping edge, this outer surface so formed that when cut by a theoretical plane parallel to the pry edge a line is defined on the outer surface which is at least substantially parallel to the cutting edge; (d) a relief portion formed on the inner portion of the jaw and with said outer surface forming this chisel edge with an acute angle of less than 90°, and when the pry and scraping edges of the opposed jaws are brought to a closed condition that outer surface adjacent the pry edge defines an acute angle such as five to fifteen degrees to a tangent line normal to a plane passing midway of the jaws and through the common engagement of the sharpened pry edges of the jaws, the cross section through a distal jaw portion being of increasing thickness beginning at the sharp chisel edge and moving away therefrom, the combined relief portions formed in the jaw portions sufficient for the jaws to be brought substantially together in a pry and scraping action with the removed bracket in the relief portions, and (e) a partially resilient cap member having an interior portion so formed as to be tightly although removably mountable on the distal and sharpened chisel end of the jaw, this cap member adapted to cover this distal hardened chisel jaw end and to be intimately supported by the inner relief configuration, the supported cap member when and while in this mounted condition is adapted to be placed on the upper surface of a tooth, said cap when so positioned providing a support enabling the chisel edge of the uncapped jaw to be manipulated to pry an adhesively attached bracket and/or the residue cement from the face of the tooth to which the bracket was attached.

2. An orthodontic tool as in claim 1 in which the outer surface adjacent and terminating with the sharpened chisel edge of the jaws is a planar surface.

3. An orthodontic tool as in claim 1 in which the jaws are like hardened inserts and are mounted as mirror images of each other.

4. An orthodontic tool as in claim 3 in which the jaws are displaced from 20° to 60° from alignment with the nominal longitudinal axes of the handles.

5. An orthodontic tool as in claim 1 in which the semiresilient cap protective member is molded of Teflon.

6. An orthodontic tool as in claim 1 in which a spring clip is provided and secured to one of the handle members in such a manner to enable the tool to be used while the semirigid cap member is stored on the clip during those periods the cap is not in use.

7. An orthodontic tool as in claim 1 in which the outer side edges of the outer surface are formed with sharpened portions so as to provide additional scraping means for the removal of adhesive residue.

* * * * *